United States Patent [19]

Shiozawa et al.

[11] Patent Number: 4,888,436

[45] Date of Patent: Dec. 19, 1989

[54] PROCESS FOR PREPARING AMINOPROPYL ALKOXY SILANES

[75] Inventors: Kouji Shiozawa, Saitama; Haruko Takai, Chiba; Kazutoshi Takatsuna; Nobukazu Okamoto, both of Saitama; Yoshiharu Okumura, Tokyo; Chihiro Imai, Kanagawa, all of Japan

[73] Assignee: Toa Nenryo Kogyo Kabushiki Kaisha, Tokyo, Japan

[21] Appl. No.: 174,493

[22] Filed: Mar. 28, 1988

[30] Foreign Application Priority Data

Mar. 27, 1987 [JP] Japan ............................. 62-73489
May 15, 1987 [JP] Japan ........................... 62-1181138
Aug. 11, 1987 [JP] Japan ........................... 62-200234
Dec. 16, 1987 [JP] Japan ........................... 62-318402

[51] Int. Cl.$^4$ ............................................ C07F 7/10
[52] U.S. Cl. ............................... 556/413; 556/424
[58] Field of Search ................................ 556/413, 424

[56] References Cited

U.S. PATENT DOCUMENTS 4,481,364 11/1984 Chu et al. ........................ 556/413
4,556,722 12/1985 Quirk et al. ..................... 556/413

Primary Examiner—Paul F. Shaver
Attorney, Agent, or Firm—Wenderoth, Lind & Ponack

[57] ABSTRACT

A process for preparing aminopropyl alkoxy silanes comprising reacting an allylamine having at least one active hydrogen atom attached to the amine nitrogen atom with a hydro-alkoxy silane having from 1 to 3 alkoxy groups attached to the silicon atom in the presence of a rhodium complex having inorganic ligands, at least one of said ligands being carbonyl. By this process the desired gamma-isomer can be prepared in a high selectivity and yield within a short reaction time. When the reaction is carried out in the presence of carbon monoxide and/or a cyclic olefinic compound, the selectivity and yield of the gamma-isomer can be further improved. The presence of carbon monoxide in the reaction system further serves to lengthen the catalyst life and to reduce the amount of the catalyst to be used.

7 Claims, No Drawings

PROCESS FOR PREPARING AMINOPROPYL ALKOXY SILANES

TECHNICAL FIELD OF THE INVENTION

The present invention relates to a process for preparing aminopropyl alkoxy silanes. More particularly, it relates to a process for preparing aminopropyl alkoxy silanes wherein an allylamine having at least one active hydrogen atom attached to the amine nitrogen atom is reacted with a hydro-alkoxy silane using as a catalyst a rhodium complex having inorganic ligands, at least one of which is CO. Such a rhodium catalyst, which may be briefly referred to herein as a rhodium carbonyl complex, will be described hereinafter in detail. As known in the art, the aminopropyl alkoxy silanes are useful as silane coupling agents.

BACKGROUND OF THE INVENTION

Silane coupling agents are compounds having in their molecule an organic functional group and a hydrolizable group reactive with organic materials. Since the silane coupling agents are, due to their functional groups, capable of chemically bonding an organic polymer with an inorganic material, such as silica, thereby remarkably increasing the mechanical strength of the organic polymer, demand of them is increasing as an indispensable material in the development of ultrafashionable composite materials.

Gamma-aminopropyl alkoxy silanes are used in the art as silane coupling agents, and it is known that they can be prepared by hydrosililation of an allylamine, which may be substituted on the nitrogen atom, with a hydro-alkoxy silane.

For example, Japanese Patent Laid-open Publication No. 60-81189 discloses a process for the preparation of aminopropyl alkoxy silanes, which comprises reacting an allylamine with a hydro-alkoxy silane using a platinum catalyst, such as chloroplatinic acid, in the presence of a promoter, such as anhydrous sodium carbonate. However, the reaction of an allylamine with a hydro-alkoxy silane in the presence of a platinum catalyst, such as chloroplatinic acid, inevitably produces the corresponding beta-aminopropyl alkoxy silane, which may be referred to herein as the beta-isomer in addition to the desired gamma-aminopropyl alkoxy silane, which may be referred to herein as the gamma-isomer, normally with a ratio of the gamma-isomer to the beta-isomer of from 4 to 6, posing a problem in that the selectivity of the desired gamma-isomer is not satisfactorily high.

Japanese Patent Laid-open Publication No. 61-229885 discloses a process for the preparation of aminopropyl alkoxy silanes by reacting an allylamine with a hydro-alkoxy silane in the presence of a catalyst comprising rhodium organic tertiary phosphine complex and optionally triphenylphosphine. By this process gammma-aminopropyl alkoxy silanes can be prepared in a high selectivity. The process is disadvantageous, however, in that a prolonged reaction time is required to achieve a high conversion, and an excessive amount of triphenylphosphine must be used to achieve a high selectivity of the gamma-isomer.

J. of Organomet. Chem., 149, 29–36 (1978) deals with the hydrosililation of olefins in the presence of a metallic carbonyl catalyst, such as cobalt-, rhodium-, iridium- and iron-carbonyl compounds and reports that N,N-dimethylaminopropyl triethoxy silane is obtainable in a high yield from N,N-dimethylallylamine and triethoxy silane. It is stated in this article that when an olefinic amine, such as allylamine, is hydrosililated, the sililation proceeds preferentially on the amine nitrogen atom. This statement means that the metallic carbonyl compounds, such as rhodium carbonyl would be unsuitable as a catalyst for the preparation of an aminopropyl alkoxy silane by hydrosililating an allylamine having at least one active hydrogen atom attached to the amine nitrogen atom with a hydro-alkoxy silane.

OBJECT OF THE INVENTION

The invention is to solve the problems involved in the prior art and an object of the invention is to provide a process for preparing aminopropyl alkoxy silanes from a hydro-alkoxy silane and an allylamine having at least one active hydrogen atom attached to the amine nitrogen atom, in a high selectivity and yield within a shortened reaction time.

SUMMARY OF THE INVENTION

A process for preparing aminopropyl alkoxy silanes according to the invention comprises reacting an allylamine of the formula [I]

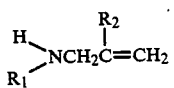
[I]

wherein $R_1$ is hydrogen, alkyl having from 1 to 10 carbon atoms, alkenyl having from 2 to 10 carbon atoms, phenyl, substituted phenyl, $-CH_2CH_2NHCH_2CH_2NH_2$ or $-CH_2CH_2NH_2$, and $R_2$ is hydrogen or alkyl having from 1 to 6 carbon atoms with a hydro-alkoxy silane of the formula [II]

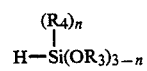
[II]

wherein $R_3$ and $R_4$ are the same or different, each being alkyl having from 1 to 6 carbon atoms, and n is 0, 1 or 2, in the presence of an inorganic rhodium complex having at least one carbonyl ligand.

The reaction according to the invention may be carried out in the presence of carbon monooxide or a cyclic olefinic compound. By doing so the selectivity and yield of the gamma-isomer may be further improved. The presence of carbon monoxide in the reaction system further serves to lengthen the catalyst life and to reduce the amount of the catalyst to be used.

DETAILED DESCRIPTION OF THE INVENTION

A process for preparing aminopropyl alkoxy silanes according to the invention will be fully described hereinafter.

Allylamines

Allylamines having at least one active hydrogen atom attached to the amine nitrogen atom, as represented by the formula [I], can be used herein.

Examples of such allylamines include, for example, allylamine, N-methylallylamine, N-ethylallylamine, 2-methylallylamine, diallylamine and allylethylenediamine.

Hydro-alkoxy silanes

Hydro-alkoxy silanes having from 1 to 3 alkoxy groups attached to the silicon atom, as represented by the formula [II] can be used herein. Of these, hydro-alkoxy silanes of the formula [II] wherein n is 0 or 1, and $R_3$ and $R_4$ each represents methyl or ethyl, are preferred.

Examples of hydro-alkoxy silanes of the formula [II] include, for example, triethoxy silane, trimethoxy silane, tripropoxy silane, tributoxy silane, methyl dimethoxy silane, ethyl dimethoxy silane, methyl diethoxy silane, dimethyl methoxy silane, trioctyloxy silane, methyl dioctyloxy silane and dimethyl octyloxy silane.

Rhodium carbonyl complex

When an allylamine as described above is reacted with a hydro-alkoxy silane as described above according to the invention, use is made, as a catalyst, of a rhodium carbonyl complex having inorganic ligands, at least one of said inorganic ligands being carbonyl. The remaining inorganic ligands possessed by the complex may also be carbonyl, but they may be hydrogen, sulfur, carbon, amine, nitrile, chlorine and thiocarbonyl.

Examples of suitable rhodium carbonyl complexes include:

(1) [0] valent rhodium carbonyl complexes, such as $Rh_2(CO)_8$, $Rh_4(CO)_{12}$ and $Rh_6(CO)_{16}$;

(2) anionic rhomdium carbonyl complexes, such as $Rh(CO)^{4-}$, $[Rh_4(CO)_{11}]^{2-}$, $[Rh_6(CO)_{15}]^{2-}$, $[Rh_6(CO)_{14}]^{4-}$, $[Rh_7(CO)_{16}]^{3-}$ and $[Rh_{12}(CO)_{30}]^{2-}$, coupled with (equivalent) cations, such as ammonium, quarternary ammonium, e.g. tetraalkylammonium, and alkali metal ions;

(3) rhodium carbonyl complexes having hetero atoms, such as $Rh_{12}(CO)_{25}(C)_2$, and $Rh_8(CO)_{19}C$; and;

(4) other rhodium carbonyl complexes, such as $[Rh_6(CO)_{15}C]^{2-}$, $[Rh_{17}(CO)_{32}(S)_2]^{3-}$, $HRh(CO)_4$, $[H_3Rh_{13}(CO)_{24}]^{2-}$ and $[H_2Rh_{13}(CO)_{24}]^{3-}$.

Rhodium carbonyl complex, which can be used herein, are inorganic in that they are free from any organic ligand, such as triphenylphosphine.

The rhodium carbonyl complex may be separately prepared and the catalyst so prepared may be added to the reaction system, or it may be formed in the reaction system and the complex so formed in situ may be used as the catalyst.

Reaction conditions

The allylamine and hydro-alkoxy silane are preferably used in such amounts that a ratio of the allylamine to the hydro-alkoxy silane by mole is within the range from about 1.3:1 to about 1:1:3.

The reaction may be carried out under atmospheric or elevated pressure. The reaction is normally carried out at a temperature of from about 50° C. to about 250° C. If the reaction temperature substantially below 50° C. is used, the desired gamma-isomer will be formed in little amounts. Whereas, as the reaction temperature exceeds about 250° C., increasing amounts of the beta-isomer tend to be formed, undesirably lowering the selectivity of the gamma-isomer. Preferred reaction temperatures are from about 100° C. to about 200° C.

While the rhodium carbonyl complex may be used in an excess amount, it is sufficient for it to be present in the reaction system in an amount on the order of from $10^{-7}$ to $10^{-3}$ mole per mole of the allylamime, on a rhodium basis.

In carrying out the reaction, solvents may or may not be used. When solvents are used, generally, hydrocarbon solvents, such as toluene, xylene, heptane and dodecane are preferred.

While the reaction time greatly depends upon the reaction temperature used, it may normally be within the range between about 0.5 and about 2.0 hours.

When an allylamine is reacted with a hydro-alkoxy silane in the presence of a rhodium carbonyl complex in accordance with the invention, the corresponding gamma-aminopropyl alkoxy silane can be produced in a high selectivity. For example, the gamma-isomer can be produced with a gamma/beta ratio as high as 15 to 16. Further, the reaction rapidly proceeds, and thus, the gamma-isomer can be obtained in a yield as high as 50 to 70%.

In contrast, if an allylamine is reacted with a hydroalkoxy silane, using a chloroplatinic acid catalyst, the yield of the gamma-isomer is on the order of 40–50%, with a gamma/beta ratio of about 4. Further, if an allylamine is reacted with a hydro-alkoxy silane, using rhodium hydride carbonyl tris(triphenylphosphine) complex as a catalyst, the gamma-isomer with a high gamma/beta ratio can only be obtained at the cost of a prolonged reaction time, e.g., 6 hours, owing to a slow reaction velocity.

The reaction of an allylamine with a hydro-alkoxy silane, described above, may be carried out in the presence of carbon monoxide, whereby the selectivity and yield of the gamma-isomer may be further improved and the life of the catalyst may be remarkably lengthened, and the amount of the catalyst to be used may be greatly reduced. In fact the reaction may effectively proceed in the presence of carbon monoxide even with a minimum amount of the catalyst, with which the reaction does not substantially proceed in the absence of the carbon monoxide.

To carry out the reaction in the presence of carbon monoxide, it is necessary to forcibly add the carbon monoxide to the reaction system from the exterior. This may be done either by flowing carbon monoxide through a reaction vessel during the reaction, or by charging the reaction vessel with an appropriate amount of carbon monoxide under pressure prior to the reaction.

The reaction of an allylamine with a hydro-alkoxy silane, described above, may be carried out in the presence of a cyclic olefinic compound, whereby the selectivity and yield of the gamma-isomer may be further improved. Further, if carbon monoxide co-exists together with the cyclic olefinic compound in the reaction system, the selectivity and yield of the gamma-isomer may be greatly improved and the life of the catalyst may be remarkably lengthened, and the amount of the catalyst to be used may be greatly reduced.

Of the cyclic olefinic compounds, those having at least 5 carbon atoms and at least one double bond in the molecule are preferred. Examples of such cyclic olefins include, for example, monocyclic olefins, such as cyclopentene, cyclopentadiene, cyclohexene, cyclohexadiene, cycloheptene, cycloheptadiene, cycloheptatriene, cyclooctene, cyclooctadiene, cyclooctatriene and cyclooctatetraene; and condensed binuclear olefins, such as, norbornene and norbornadiene.

When the cyclic olefinic compound is used, it is added to the reaction system preferably in an amount of from about 1 to about 1000 moles, more preferably from about 10 to about 100 moles per mole of the rhodium carbonyl complex used as the catalyst.

The presence of the cyclic olefinic compound, in the reaction system, in the amount described above suppresses the formation of by-products other than aminopropyl alkoxy silanes, whereby the yield of the gamma-aminopropyl alkoxy silane is greatly improved.

Since the cyclic olefinic compound is not very reactive, almost all of the cyclic olefinic compound added to the reaction sytem remains unchanged after the reaction has been completed. If desired, the cyclic olefinic compound remaining in the reaction system after the reaction may be recovered for re-use.

Effects of the Invention

By a process for preparing aminopropyl alkoxy silanes according to the invention, in which an allylamine having at least one active hydrogen atom attached to the amine nitrogen atom is reacted with a hydro-alkoxy silane in the presence of a rhodium carbonyl complex having inorganic ligands, at least of said ligand being carbonyl, the corresponding gamma-aminopropyl alkoxy silane can be prepared in a high selectivity and yield within a short period of reaction time.

When the reaction described above is carried out in the co-presence of carbon monoxide and/or a cyclic olefinic compound, the selectivity and yield of the gamma-isomer can be greatly improved. In addition, the presence of carbon monoxide in the reaction system serves to remarkably lengthen the catalyst life and to greatly reduce the amount of the catalyst to be used.

While the invention is illustrated by the following examples, the invention is not limited thereto.

EXAMPLE 1

A three-neck flask equipped with a reflux condenser, stirring rod and thermometer was charged with 14 grams of allylamine (0.25 mole), 41 grams of triethoxy silane (0.25 mole) and 30 ml. of toluene, and heated in an oil bath maintained at a temperature of 110° C. When the temperature of the mixture reached 85° C., 0.22 gram of tetrarhodium dodecacarbonyl was added to the mixture as a catalyst. About 30 minutes after the addition of the catalyst, the reaction temperature reached 110° C. At the end of the period the reaction mixture was subjected to gas chromatography analysis. It was found that gamma-aminopropyl triethoxy silane was obtained in a yield of 68% on an allylamine basis, while the yield of beta-aminopropyl triethoxy silane was 4.9% on an allylamine basis.

EXAMPLE 2

The reaction of allylamine with triethoxy silane as in Example 1 was repeated, except that 0.3 gram of hexarhodium hexadecacaronyl was used as a catalyst, and xylene was used as a solvent, with other conditions remaining the same. After the completion of the reaction, the reaction mixture was subjected to gas chromatography analysis. It was found that the gamma-isomer was obtained in a yield of 71% on an allylamine basis, while the yield of the beta-isomer was 4.4% on an allylamine basis.

EXAMPLE 3

The reaction of allylamine with triethoxy silane as in Example 1 was repeated, except that 0.38 gram of a tetraethylammonium salt of hexarhodium pentadecacaronyl was used as a catalyst, and xylene was used as a solvent, with other conditions remaining the same. After the completion of the reaction, the reaction mixture was subjected to gas chromatography analysis. It was found that the gamma-isomer was obtained in a yield of 51% on an allylamine basis, while the yield of the beta-isomer was 3.5% on an allylamine basis.

EXAMPLE 4

Example 1 was repeated except that the 41 grams of triethoxy silane was replaced with 30.6 grams of trimethoxy silane (0.25 mole) and the catalyst was used in an amount of 0.2 gram. After the completion of the reaction, the reaction mixture was subjected to gas chromatography analysis. It was found that gamma-aminopropyl trimethoxy silane was obtained in a yield of 62% on an allylamine basis, while the yield of beta-aminopropyl triethoxy silane was 4.0% on an allylamine basis.

EXAMPLE 5

A three-neck flask equipped with a reflux condenser, stirring rod and thermometer was charged with 25 grams of allylethylenediamine (0.25 mole), 41 grams of triethoxy silane (0.25 mole) and 30 ml. of n-dodecane and heated in an oil bath maintained at a temperature of 150° C. When the temperature of the mixture reached 130° C., 0.1 gram of tetrarhodium dodecacarbonyl was added to the reaction mixture as a catalyst. After the temperature of the reaction mixture had reached 150° C., the mixture was maintained at this temperature for 30 minutes. After the completion of the reaction, the reaction mixture was subjected to gas chromatography analysis. It was found that gamma-ethylenediaminopropyl triethoxy silane was obtained in a yield of 63% on an allylethylenediamine basis.

EXAMPLE 6

The reaction of allylamine with triethoxy silane as in Example 1 was repeated, except that 0.41 gram of a tetraethylammonium salt of rhodium tetracarbonyl was used as a catalyst, and instead of the toluene xylene was used as a solvent, with other conditions remaining the same. After the completion of the reaction, the reaction mixture was subjected to gas chromatography analysis. It was found that the gamma-isomer was obtained in a yield of 65% on an allylamine basis, while the yield of the beta-isomer was 4.3% on an allylamine basis.

EXAMPLE 7

The reaction of allylamine with triethoxy silane as in Example 1 was repeated, except that 0.251 gram of a tetraethylammonium salt of tetrarhodium undecacarbonyl was used as a catalyst, and instead of the toluene xylene was used as a solvent, with other conditions remaining the same. After the completion of the reaction, the reaction mixture was subjected to gas chromatography analysis. It was found that the gamma-isomer was obtained in a yield of 68% on an allylamine basis, while the yield of the beta-isomer was 4.4% on an allylamine basis.

COMPARATIVE EXAMPLE 1

A four-neck flask equipped with a reflux condenser, dropping funnel, stirring rod and thermometer was charged with 41 grams of triethoxy silane (0.25 mole) and a solution of chloroplatinic (IV) acid as a catalyst, in isopropyl alcohol in an amount to provide $2 \times 10^{-5}$ mole of platinum. To the mixture heated in an oil bath maintained at a temperature of 120° C., 14 grams of allylamine (0.25 mole) was dropwise added over one hour from the dropping funnel. The mixture was maintained at 120° C. for 9 hours. After the completion of the reaction, the reaction mixture was subjected to gas chromatography analysis. It was found that gamma-aminopropyl triethoxy silane was obtained in a yield of 44% on an allylamine basis, while the yield of beta-aminopropyl triethoxy silane was 10% on an allylamine basis.

COMPARATIVE EXAMPLE 2

A four-neck flask equipped with a reflux condenser, dropping funnel, stirring rod and thermometer was charged with 41 grams of triethoxy silane (0.25 mole) and 1.4 grams of rhodium hydride carbonyl-tris(triphenylphosphine) as a catalyst. The mixture was heated to a temperature of 110° C. and 14 grams of allylamine (0.25 mole) was dropwise added over one hour from the dropping funnel. The mixture was maintained at 110° C. for a further hour. At the end of the period, it was revealed by gas chromatography that gamma-aminopropyl triethoxy silane was produced in a yield of 34% on an allylamine basis. The reaction mixture was maintained for further 4 hours. At the end of the period the yields of gamma- and beta-aminopropyl triethoxy silanes reached 71% and 6.9% on an allylamine basis, respectively.

EXAMPLE 8

A 200 ml. flask equipped with a stirrer, thermometer, dropping funnel, CO inlet tube and reflux condenser having a CO outlet tube, was charged with 41 grams of triethoxy silane (0.25 mole), 1.9 milligrams of tetrahodium dodecacarbonyl ($2.5 \times 10^{-6}$ mole) and 30 ml. of toluene. While passing carbon monoxide through the flask at a rate of 10 ml./min., the mixture was heated to a temperature of 110° C. under stirring. To the mixture 14 grams of allylamine (0.25 mole) was dropwise added in 2 minutes. After the addition of the allylamine the CO flush, heating and stirring were continued for 30 minutes. It was revealed by gas chromatography that gamma-aminopropyl triethoxy silane was obtained in a yield of 62% on an allylamine basis, while the yield of beta-aminopropyl triethoxy silane was 4% on an allylamine basis.

EXAMPLE 9

Example 8 was repeated except that 30 ml. of nonane was used as a solvent, the allylamine was replaced with 25 grams of N-allylethylenediamine and the reaction mixture was heated to a temperature of 150° C. instead of 120° C. Gas chromatography revealed that the yields of N-(gamma-triethoxysilylpropyl) ethylenediamine and N-(beta-triethoxysilylpropyl) ethylenediamine were 60% and 5% on a starting amine basis, respectively.

EXAMPLE 10

Example 8 was repeated except that the catalyst was replaced with 2.7 milligrams of hexarhodium hexadecacarbonyl ($2.5 \times 10^{-6}$ mole) and no solvent was used. Gas chromatography revealed that the yields of gamma- and beta-aminopropyl triethoxy silanes were 63% and 4% on a starting amine basis, respectively.

EXAMPLE 11

Example 8 was repeated except that the catalyst was replaced with 3.1 milligrams of a tetraethylammonium salt of hexarhodium pentadecacarbonyl ($2.5 \times 10^{-6}$ mole) and the triethoxy silane was replaced with 30.5 grams of trimethoxy silane which was dropwise added in admixture with the allylamine. Gas chromatography revealed that the yields of gamma- and beta-aminopropyl trimethoxy silanes were 65% and 5% on a starting amine basis, respectively.

COMPARATIVE EXAMPLE 3

Example 8 was repeated except that the carbon monoxide was not caused to flow through the flask and the reaction was carried out under an atmosphere of nitrogen sealed in the flask. It was revealed by gas chromatography that little of both the gamma- and beta-isomers had been produced.

EXAMPLE 12

A 200 ml. flask equipped with a stirrer, thermometer, dropping funnel, CO inlet tube and reflux condenser having a CO outlet tube, was flushed with carbon monoxide and charged with 1.9 milligrams of tetrarhodium dodecacarbonyl ($2.5 \times 10^{-6}$ mole), 0.027 gram of 1,5-cyclooctadiene ($2.5 \times 10^{-4}$ mole) and 60 ml. of xylene. While passing carbon monoxide through the flask at a rate of 10 ml./min., the mixture was heated to a temperature of 120° C. under stirring. To the mixture a mixture of 41 grams of triethoxy silane (0.25 mole) and 14 grams of allylamine (0.25 mole) was dropwise added over a period of 30 minutes. After the addition of the reactants, the reaction was carried out at a temperature of 120° C. for 2.5 hours under CO flush and stirring. It was revealed by gas chromatography that gamma-aminopropyl triethoxy silane was obtained in a yield of 75% on an allylamine basis, while the yield of beta-aminopropyl triethoxy silane was 7.5% on an allylamine basis.

EXAMPLE 13

Example 12 was repeated except that the catalyst was replaced with 3.0 milligrams of hexarhodium hexadecacarbonyl ($2.8 \times 10^{-6}$ mole). Gas chromatography revealed that the yields of gamma- and beta-aminopropyl triethoxy silanes were 76% and 7.4% on a allylamine basis, respectively.

EXAMPLE 14

Example 12 was repeated except that the triethoxy silane was replaced with 30.6 grams of trimethoxy silane (0.25 mole). Gas chromatography revealed that the yields of gamma- and beta-aminopropyl trimethoxy silanes were 69% and 6.5% on an allylamine basis, respectively.

EXAMPLE 15

A three-neck flask equipped with a reflux condenser, stirring rod and thermometer was charged with 14 grams of allylamine (0.25 mole), 41 grams of triethoxy silane (0.25 mole), 0.32 gram of 1,5-cycloctadiene ($2.9 \times 10^{-3}$ mole) and 30 ml. of toluene, and heated in an oil bath maintained at a temperature of 110° C. When the temperature of the mixture reached 85° C., 0.22 gram of tetrarhodium dodecacarbonyl ($2.9 \times 10^{-4}$ mole) was added to the mixture as a catalyst. About 60 minutes after the addition of the catalyst, the reaction temperature reached 110° C. At the end of the period the reaction mixture was subjected to gas chromatography analysis. It was found that gamma-aminopropyl triethoxy silane was obtained in a yield of 78% on an allylamine basis, while the yield of beta-aminopropyl triethoxy silane was 5.6% on an allylamine basis.

EXAMPLE 16

A 200 ml. flask equipped with a stirrer, thermometer, dropping funnel, CO inlet tube and reflux condenser having a CO outlet tube, was flushed with carbon monoxide, charged with 1.9 milligrams of tetrarhodium dodecacarbonyl ($2.5 \times 10^{-6}$ mole), 14 grams of allylamine (0.25 mole) and 60 ml. of xylene, and heated in an oil bath maintained at a temperature of 110° C. Thereafter, 41 grams of triethoxy silane (0.25 mole) was dropwise added to the mixture from the dropping funnel over 30 minutes. The reaction was continued at a temperature of 110° C. for 2 hours under stirring and CO flush. It was revealed by gas chromatography that gamma-aminopropyl triethoxy silane was obtained in a yield of 58% on an allylamine basis, while the yield of beta-aminopropyl triethoxy silane was 4.9% on an allylamine basis.

We claim:

1. A process for preparing aminopropyl alkoxy silanes comprising reacting an allylamine of the formula [I]

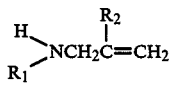
[I]

wherein $R_1$ is hydrogen, alkyl having from 1 to 10 carbon atoms, alkenyl having from 2 to 10 carbon atoms, phenyl, substituted phenyl, —$CH_2CH_2NHCH_2CH_2NH_2$ or —$CH_2CH_2NH_2$, and $R_2$ is hydrogen or alkyl having from 1 to 6 carbon atoms with a hydro-alkoxy silane of the formula [II]

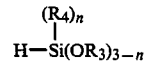
[II]

wherein $R_3$ and $R_4$ are the same or different, each represents alkyl having from 1 to 6 carbon atoms, and n is 0, 1 or 2, in the presence of a rhodium complex having inorganic ligands, at least one of said ligands being carbonyl.

2. The process in accordance with claim 1 in which the allylamine is selected from allylamine, N-methylallylamine, N-ethylallylamine, 2-methylallylamine, diallylamine and allylethylenediamine.

3. The process in accordance with claim 1 in which the hydrosilane is selected from triethoxy silane, trimethoxy silane, tripropoxy silane, tributoxy silane, methyl dimethoxy silane, ethyl dimethoxy silane, methyl diethoxy silane, dimethyl methoxy silane, trioctyloxy silane, methyl dioctyloxy silane and dimethyl octyloxy silane.

4. The process in accordance with claim 1 in which the rhodium complex is selected from tetrarhodium dodecacarbonyl, hexarhodium hexadecacarbonyl, tetraethylammonium salt of rhodium tetracarbonyl, tetraethylammonium salt of hexarhodium pentadecacarbonyl and tetraethylammonium salt of tetrarhodium undecarbonyl.

5. The process in accordance with claim 1 in which the reaction is carried out in the presence of carbon monoxide.

6. The process in accordance with claim 1 in which the reaction is carried out in the presence of a cyclic olefinic compound.

7. The process in accordance with claim 6 in which the cyclic olefinic compound is selected from cyclopentene, cyclopentadiene, cyclohexene, cyclohexadiene, cycloheptene, cycloheptadiene, cycloheptatriene, cyclooctene, cyclooctadiene, cyclooctatriene, cyclooctatetraene, norbornene and norbornadiene.

* * * * *

UNITED STATES PATENT AND TRADEMARK OFFICE
CERTIFICATE OF CORRECTION

PATENT NO. : 4,888,436

DATED : December 19, 1989

INVENTOR(S) : Kouji SHIOZAWA, Haruko TAKAI, Kazutoshi TAKATSUNA, Nobukazu OKAMOTO, Yoshiharu OKUMURA, and Chihiro IMAI It is certified that error appears in the above-identified patent and that said Letters Patent is hereby corrected as shown below:

Title page, Column 1, paragraph [30], change the Japanese Application No. "62-1181138" to -- 62-118138 --.

Signed and Sealed this

Thirtieth Day of July, 1991

Attest:

HARRY F. MANBECK, JR.

*Attesting Officer*  *Commissioner of Patents and Trademarks*